United States Patent [19]

Paul

[11] Patent Number: 5,531,988
[45] Date of Patent: Jul. 2, 1996

[54] BACTERIA AND IMMUNOGLOBULIN-CONTAINING COMPOSITION FOR HUMAN GASTROINTESTINAL HEALTH

[75] Inventor: Stephen M. Paul, San Clemente, Calif.

[73] Assignee: Metagenics, Inc., San Clemente, Calif.

[21] Appl. No.: 331,140

[22] Filed: Oct. 28, 1994

[51] Int. Cl.[6] .......................... A01N 63/04; A61K 35/00; A61K 39/395; A61K 47/00
[52] U.S. Cl. ................. 424/93.4; 424/93.45; 424/130.1; 424/234.1; 424/246.1; 424/535; 424/809; 514/21; 514/777; 514/867
[58] Field of Search ............................... 424/93.4, 93.45, 424/130.1, 133.1, 135.1, 234.1, 246.1, 535, 809; 514/21, 777, 867

[56] References Cited

U.S. PATENT DOCUMENTS

| | | | |
|---|---|---|---|
| 4,816,252 | 3/1989 | Stott et al. | 530/416 |
| 4,834,974 | 5/1989 | Stott et al. | 424/85.8 |
| 4,994,442 | 2/1991 | Gil et al. | 514/45 |
| 5,066,491 | 11/1991 | Stott et al. | 424/85.5 |
| 5,330,756 | 7/1994 | Stewart et al. | 424/405 |
| 5,413,785 | 5/1995 | Nanji | 424/93.45 |

OTHER PUBLICATIONS

Gustavo Bounous et al., The Immunoenhancing Property of Dietary Whey Protein Concentrate, 11 Clinical and Investigative Medicine 271–78 (1988).
Viki L. Hughes & Sharon L. Hillier, Microbiologic Characteristics of Lactobacillus Products Used for Colonizatoin of the Vagina, 75 Obstet. Gynecol. 244 (1990).
Jerzy Meduski, Lactobacillus Acidophilus: A Synopsis of Its Attributes, "sell sheet" published by Metagenics, Inc. (Jun. 1989).
Probioplex: Intestinal Fortitude, "sell sheet" published by Metagenics, Inc. (Jun. 1989).
SpectraPlex and *Acidophilus* Over Candida and Salmonella, "sell sheet" published by Opson Inc. (Nov. 1989).
Article "The Effect of *Lactobacillus Acidophilus* Administration Upon the Survival of Salmonella in Randomly Selected Human Carriers" by L. Alm, *Prog. Fd. Nutr. Sci.*, vol. 7, 1983, pp. 13–17.
Article "Proteolysis of Bovine Immunoglobulins" by O.de Rham, et al., *Int. Archs Allergy appl.Immun.* 55, 1977, pp. 62–69.
Article "Antagonistic Action of *Lactobacillus acidophilus* Toward Intestinal and Foodborne Pathogens in Associative Cultures" by S. E. Gilliland, et al., *Journal of Food Protection*, vol. 40, No. 12, Dec., 1977, pp. 820–823.
Article "Microbiologic Characteristics of Lactobacillus Products Used for Colonization of the Vagina" by Viki L. Hughes, MT, et al., *Obstetrics & Gynecology*, pp. 244–248.
"Remission of Diarrhoea Due to Cryptosporidiosis in an Immunodeficient Child Treated With Huyperimmune Bovine Colostrum" by S. Tzipori, et al., *British Medical Journal* vol. 293, Nov. 15, 1986, pp. 1276–1277.

"Growth of Bifidobacteria in Milk and Preparation of *Bifidobacterium Infantis* for a Dietary Adjunct" by E. B. Collins, et al., *Journal of Dairy Science* vol. 67, No. 7, 1984, pp. 1376–1380.
"The Role of Probiotics in Geriatric and Infant Nutrition" by N. Trenev, et al., *Townsend Letter for Doctors*—Jul. 1994, pp. 746–747.
"*Bifadobacterium adolescentis* as Best Probiotic Selection" *Nutritional Consultants Group, Inc.* Jun. 23, 1992, pp. 1–8.
"Antibody to Human Rotavirus in Cow's Milk" by Robert H. Yolken, et al., *The New England Journal of Medicine* vol. 312 No. 10 Mar. 7, 1985, pp. 605–610.
"Bovine Milk Immunoglobulins for Passive Immunity to Infantile Rotavirus Gastroenteritis" by Harold Brüssow, et al., *Journal of Clinical Microbiology*, vol. 25, No. 6, Jun. 1987, pp. 982–986.
"Use of Bovine Milk Concentrate Containing Antibody to Rotavirus to Treat Rotavirus Gastroenteritis in Infants" by Helmut Hilper, et al., *The Journal of Infectious Diseases*, vol. 156, No. 1, Jul. 1987, pp. 158–166.
"Protection by Milk Immunoglobulin Concentrate Against Oral Challenge with Enterotoxigenic *Escherichila Coli*" by Carol O. Tacket, et al., The New England Journal of Medicine, vol. 318, No. 19, May 12, 1988, pp. 1240–1243.
"Estimation of Circulating Immune Complexes following Oral Challenge with Cow's Milk in Patients with IgA Nephropathy" by Masashi Sato, et al., *Nephron* 47, 1987, pp. 43–48.
"Dietary Bovine Antigens and Immune Complex Formation After Intravenous Immunoglobulin in Common Varied Immunodeficiency" by C. Cunningham–Rundles, et al., *Journal of Clinical Immunology*, vol. 6, No. 5, 1986, pp. 381–388.
"Treatment of Infantile *E. coli* Gastroenteritis with Specific Bovine anti–*E. coli* Milk Immunoglobulins" by C. Mietens, et al., *European Journal of Pediatrics*, 132, 1979, pp. 239–252.
"Passive Immunity to Bovine Ratavirus Infection Associated with Transfer of Serum Antibody into the Intestinal Lumen" by Thomas E. Besser, et al., *Journal of Virology*, vol. 62, No. 7, Jul. 1988, pp. 2238–2242.
"Yogurt—an Autodigesting Source of Lactose" by Joseph C. Kolars, M.D., et al., *The New England Journal of Medicine*, vol. 310, No. 1, Jan. 5, 1984, pp. 1–3.

(List continued on next page.)

*Primary Examiner*—Nathan M. Nutter
*Attorney, Agent, or Firm*—Thorpe, North & Western

[57] ABSTRACT

A composition for promoting gastrointestinal health comprises an effective amount of a beneficial human intestinal microorganism and an effective amount of an immunoglobulin composition comprising concentrated immunologically active immunoglobulins. Preferred beneficial human intestinal bacteria include lactobacilli and bifidobacteria. The immunologically active immunoglobulins are preferably purified from bovine milk, milk products, or whey. Methods of use are also described.

35 Claims, 3 Drawing Sheets

OTHER PUBLICATIONS

"Protein–Mediated Adhesion of *Lactobacillus* acidophilus BG2FO4 on Human Enterocyte and Mucus–Secreting Cell Lines in Culture" by Marie–Hélène Coconnier, et al., *Applied and Environmental Microbiology*, vol. 58, No. 6, Jun. 1992, pp. 2034–2039.

"Factors to Consider when Selecting a Culture of *Lactobacillus acidophilus* as a Dietary Adjunct to Produce a Hypocholesterollemic Effect in Humans": by S. E. Gilliland, et al., *Journal of Dairy Science*, vol. 73, No. 4, 1990, pp. 905–911.

"Ingestion of Yogurt Containing *Lactobacillus acidophilus* as Prophylaxis for Candidal Vaginitis" by Eileen Hilton, MD, et al., *American College of Physicians*, Mar. 1, 1992, vol. 116, No. 5, pp. 353–357.

"Inhibition of *Candida albicans* by *Lactobacillus acidophilus*" by E. B. Collins, et al., *Journal of Dairy Science*, vol. 63, No. 5, 1980, pp. 830–832.

"Adherence of Lactobacillus Species to Human Fetal Intestinal Cells" by E. G. Kleeman, et al., *Journal of Dairy Science*, vol. 65, No. 11, 1982 pp. 2063–2069.

"Contribution of the Microflora of the Small Intestine to the Vitamin $B_{12}$ Nutriture of Man" by V. Herbert, et al., *Nutrition Reviews*, vol. 38, No. 8, Aug. 1980, pp. 274–275.

"Beneficial Effects of Administration of *Lactobacillus Acidophilus* in Diarrheal and Other Intestinal Disorders" by Charles Beck, M.D., et al., *The American Journal of Gastroenterology*, vol. 35, 1961, pp. 522–530.

"*Lactobacillus Acidophilus*: Method of Action, Clinical Application, and Toxcity Data" by Alexander G. Schauss, *Journal of Advancement in Medicine* (In Press) 1990, pp. 1–12.

BACTERIA AND IMMUNOGLOBULIN-CONTAINING COMPOSITION FOR HUMAN GASTROINTESTINAL HEALTH

BACKGROUND OF THE INVENTION

This invention relates to a bacteria- and immunoglobulin-containing composition and methods of use thereof for promoting gastrointestinal health. More particularly, the invention relates to a composition comprising living bacteria that are beneficial for gastrointestinal health and an immunoglobulin preparation containing immunoglobulins that are capable of binding and inactivating foreign antigens such as pathogenic bacteria, viruses, fungi, and protozoa that are detrimental to gastrointestinal health.

Since the time of Hippocrates and throughout the Middle Ages, large doses of whey were prescribed by alchemists for treating many ailments, primarily acute septic conditions. Although it was not then known the reason that whey was useful for treating such conditions, recent studies have shown that whey contains antibodies or immunoglobulins capable of providing passive immunity against various pathogens and their toxic by-products. Antibodies or immunoglobulins are high molecular weight proteins produced in the bodies of mature animals that enhance immunity to infection by bacteria, viruses, fungi, protozoa, and the like. Antibodies in human and bovine milk promote development of a healthy gastrointestinal tract and provide protection against infections by pathogenic microorganisms. These antibodies interfere with the process that allows such pathogenic microorganisms to adhere to and colonize the intestinal lining. Studies have shown that immunoglobulins from whey are particularly effective against viruses (e.g. rotavirus), bacteria (*E. coli, Vibrio cholerae,* Salmonella), fungi (Candida), and protozoa (Cryptosporidium).

Detectable levels of anti-rotavirus antibodies ($IgG_1$) have been found in raw and pasteurized milk. R. H. Yolken, Antibody to Human Rotavirus in Cow's Milk, 312 New Eng. J. Med. 605 (1985). The high temperatures used in processing infant formula, however, destroy all traces of naturally occurring $IgG_1$. Many infants develop gastroenteritis around 6 months of age, about the time they are weaned from breast milk and started on formula.

Since infants and young children are highly susceptible to gastroenteritis, treatment of acute diarrhea with concentrated immunoglobulins has been investigated. In one study, infants hospitalized with acute rotavirus gastroenteritis were treated with an immunoglobulin concentrate derived from rotavirus-immunized cows. H. Hilpert et al., Use of Bovine Milk Concentrate containing Antibody to Rotavirus to Treat Rotavirus Gastroenteritis in Infants, 156 J. Infect. Dis. 158 (1987). These infants showed significantly reduced duration of rotavirus excretion. Thus, bovine milk immunoglobulin provided passive immunity against rotavirus gastroenteritis in human infants.

A bovine milk immunoglobulin concentrate derived from *E. coli*-immunized cows has also been shown to inhibit colonization of enteropathic *E. coli* in affected infants. C. Mietens et al., Treatment of Infantile E. Coli Gastroenteritis with Specific Bovine Anti-*E. Coli* Milk Immunoglobulins, Eur. J. Pediatrics (1979). Stool samples showed a reduction in *E. coli* counts and the duration of diarrhea was shortened, demonstrating that this concentrate was effective in treating infantile diarrhea.

Inflammation of the gastrointestinal mucosa and diarrhea associated with Traveler's Diarrhea due to *E. coli* infection have been prevented by treatment with an immunoglobulin concentrate from bovine milk. C. Tackether al., Protection by Milk Immunoglobulin Concentrate against Oral Challenge with Enterotoxigenic Escherichia Coli, 318 N. Engl. J. Med. 1240 (1988).

Immunoglobulins from bovine colostrum have been shown to be an effective treatment for diarrhea due to a pathogenic protozoan, Cryptosporidium. S. Tzipori et al., Remission of Diarrhoea Due to Cryptosporidiosis in an Immunodeficient Child Treated with Hyperimmune Bovine Colostrum, 293 Br. Med. J. 1276 (1986). Immunodeficient individuals, particularly those with acquired immune deficiency syndrome (AIDS) are especially susceptible to cryptosporidiosis.

Certain bacteria have also been shown to be beneficial to human gastrointestinal health. Bacteria of the genus Lactobacillus have been used for several hundred years for treating various illnesses. Lactobacilli found in the human intestinal tract include *L. acidophilus, L. casei, L. fermentum, L. salivaroes, L. brevis, L. leichmannii, L. plantatum,* and *L. cellobiosus.* In recent years, *L. acidophilus* has been shown to be exceptionally useful in treating conditions such as antibiotic-induced imbalances in the gastrointestinal microflora, hypercholesterolemia, vaginal infections, *E. coli* infection, oral contraceptive failure, depressed immunity, cancerous tumors, chronic granulomatous disease, and lactose indigestion. A. G. Shauss, Method of Action, Clinical Application, and Toxicity Data, 3 J. Advancement Med. 163 (1990). In vitro studies have shown *L. acidophilus* to have an inhibitory effect on the growth of pathogenic bacteria such as *Campylobacter pylori, Staphylococcus aureus, Pseudomonas aeruginosa,* and *Sarcina lutea.* K. M. Shahani et al., Natural Antibiotic Activity of Lactobacillus Acidophilus and Bulgaricus, 11 Cultured Dairy Products J. 14 (1976).

The beneficial effect of *L. acidophilus* is further illustrated by preliminary evidence that *L. acidophilus* inhibits the toxic activities of bacteria in patients with chronic kidney failure. M. L. Simenhoff et al., Biomodulation of Uremic Pathophysiology in Man, abstract presented at Am. Soc. of Nephrology Meeting, Baltimore, 1992. Such patients often have toxic levels of amines in their blood due to bacterial overgrowth in the small bowel. Consumption of high levels of freeze dried bacteria drastically reduced levels of these toxic amines. These results demonstrate the ability of *L. acidophilus* to exert a positive effect on the microflora of the intestines.

It has also been shown that the activities of fecal bacterial enzymes thought to play a role in conversion of procarcinogens to carcinogens, such as beta-glucuronidase, nitroreductase, and azoreductase, were reduced 2- to 4-fold in subjects taking *L. acidophilus* supplements. B. R. Goldin & L. S. Gorbach, The Effect of Milk and Lactobacillus Feeding on Human Intestinal Bacterial Enzyme Activity, 39 Amer. J. Clin. Nutr. 756 (1984). These results suggest that dietary supplementation with *L. acidophilus* may reduce the risk of developing colon cancer.

Bifidobacteria are also known to exert a beneficial influence on human health. These bacteria exert antimicrobial activity in the human intestine by producing lactic acid and acetic acid as a result of carbohydrate metabolism. These acids lower the intestinal pH, thereby inhibiting overgrowth of gastrointestinal pathogens. Therapeutic applications of bifidobacteria are indicated for the management of diarrhea and constipation, and the management of hepatic encephalopathy with hyperammonemia. Additional benefits include the production of B vitamins and breakdown of carcinogenic N-nitrosamines.

*Bifidobacterium adolescentis* is the predominant species of bacteria in humans after age two. This predominance suggests its exceptional stability and prolonged proliferation in the intestine. Nevertheless, for any preparation of living microorganisms to function as a commercial dietary supplement, in addition to being able to provide a beneficial effect must also exhibit good survival in storage, resistance to inactivation by bile, and survival through the gastrointestinal tract. Strain-to-strain or isolate-to-isolate variability can occur as to these traits, thus the selected properties should be verified before commercializing any particular product containing such microorganisms.

In view of the foregoing, it will be appreciated that a composition for improving gastrointestinal health comprising living bacteria that exert a beneficial effect on the gastrointestinal tract and an immunoglobulin preparation containing immunoglobulins that bind and inactivate pathogenic microorganisms in the gastrointestinal tract would be a significant advancement in the art.

OBJECTS AND SUMMARY OF THE INVENTION

It is an object of the present invention to provide a composition for use as a dietary supplement that benefits human gastrointestinal health when administered orally.

It is also an object of the invention to provide a composition for use as a dietary supplement comprising living intestinal microorganisms that aid in restoring and maintaining a healthy gastrointestinal environment.

It is another object of the invention to provide a composition for use as a dietary supplement comprising living intestinal microorganisms that are resistant to inactivation by exposure to bile.

It is still another object of the invention to provide a composition for use as a dietary supplement comprising living intestinal microorganisms that are stable upon storage at room temperature.

It is yet another object of the invention to provide a composition for use as a dietary supplement comprising living intestinal microorganisms and immunologically active immunoglobulins that is effective for treating ailments due to gastrointestinal pathogens such as bacteria, viruses, fungi, or protozoa.

It is also an object of the invention to provide a composition for use as a dietary supplement that is effective for treating diarrhea.

It is another object of the invention to provide a composition for reducing the titer of a pathogenic microorganism in the gastrointestinal tract.

These and other objects may be accomplished by providing a composition for use as a dietary supplement for promoting gastrointestinal health comprising an effective amount of a beneficial human intestinal microorganism and an effective amount of an immunoglobulin composition comprising concentrated immunologically active immunoglobulins. Such immunoglobulins may be obtained from any viable source, but are preferably obtained from bovine milk or a milk product. Most preferably, such immunoglobulins are purified from whey. The beneficial human intestinal microorganism is selected from the group consisting of lactobacilli and bifidobacteria. *Lactobacillus acidophilus* and *Bifidobacterium adolescentis* are preferred, and *L. aci-dophilus* strain NCFM is more preferred. The immunoglobulin composition can further comprise an inert carrier, such as a carbohydrate and/or a lipid.

A method of promoting gastrointestinal health comprises the step of orally administering an effective amount of the bacteria and immunoglobulin-containing composition described above. This method is also effective against bacteria, viruses, fungi, and protozoa that cause diarrhea, constipation, and other forms of gastrointestinal distress.

Brief Description of the Drawings FIG. 1 shows growth curves for Candida (●) cultured alone, and for a mixed culture of Candida (♦) and *L. acidophilus* NCFM (▲).

DETAILED DESCRIPTION OF THE INVENTION

Figure 1:
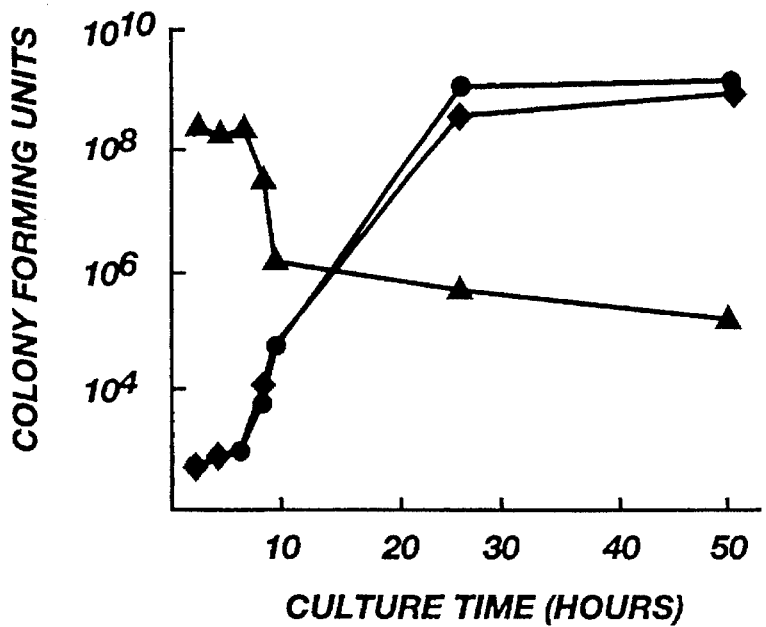

Before the present composition and methods of use are disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the content clearly dictates otherwise. Thus, for example, reference to a composition containing "a microorganism" includes a mixture of two or more microorganisms, reference to "an immunoglobulin" includes reference to two or more of such immunoglobulins, and reference to "a concentrate" includes reference to a mixture of two or more concentrates.

In describing and claiming the present invention, the following terminology will be used in accordance with the definitions set out below.

As used herein, "immunoglobulin composition" means a composition comprising an effective amount of immunologically active immunoglobulins. Preferably, these are present as concentrated immunologically active immunoglobulins. One such immunoglobulin composition is sold under the trademark "PROBIOPLEX" by Metagenics, Inc. (San Clemente, Calif.). PROBIOPLEX contains (1) about 55–60 parts by weight of an immunoglobulin concentrate from bovine whey wherein at least about 7% by weight of the total solids in the concentrate is immunologically active immunoglobulins, (2) about 35–40 parts by weight of a mixture of carbohydrates including rice maltodextrin and lactose, and (3) about 5–10 parts by weight of lipid including lecithin. Thus, at least about 3.6% by weight of the total PROBIOPLEX composition comprises immunologically active immunoglobulins. The carbohydrates and lipids function as inert carriers for the immunoglobulins. The rice maltodextrin further functions as an energy source for the beneficial microorganisms with which the immunoglobulin composition is mixed in accordance with the present invention. The lecithin aids in dispersion of the powder form of the immunoglobulin composition when reconstituted with water or other liquid. Although PROBIOPLEX contains ingredients other than concentrated immunologically active immunoglobulins, these other ingredients are optional components of the invention. What is required is that the composition contain an "effective amount" of immunologically active immunoglobulins that are preferably present in concentrated form.

As used herein, "beneficial human intestinal microorganism" means an organism of microscopic size, such as a bacterium, that inhabits the human intestine and exerts a beneficial effect on the gastrointestinal health of an individual in which it resides. Preferred beneficial human intestinal microorganisms according to the present invention include bacteria of the genera Lactobacillus and Bifidobacterium. An especially preferred lactobacillus is L. acidophilus, and an especially preferred bifidobacterium is B. adolescentis. Other lactobacilli that are beneficial to gastrointestinal health include L. acidophilus, L. bulgaricus, L. casei, L. fermentum, L. salivaroes, L. brevis, L. leichmannii, L. plantarum, and L. cellobiosus. Other bifidobacteria that are beneficial to gastrointestinal health include B. infantis, B. longum, B. thermophilum, and B. bifidum.

As used herein, "effective amount" means an amount necessary to achieve a selected result. For example, an effective amount of an immunoglobulin and bacteria containing composition useful for reducing the titer of a selected pathogenic microorganism in the gastrointestinal tract would be an amount that achieves the selected result of reducing the titer of the microorganism. Such an amount can be readily determined without undue experimentation by a person of ordinary skill in the art.

As reviewed above, immunoglobulin concentrates from milk can contain immunologically active immunoglobulins that are capable of binding pathogenic microorganisms such as bacteria, viruses, fungi, and protozoa. Such immunoglobulin concentrates can be prepared from any starting material containing sufficient concentrations of immunologically active immunoglobulins, such as milk, whey, blood, and the like. An economically viable source of such immunoglobulins is the whey byproduct of the cheese making process. It has been estimated that approximately 85 million metric tons of whey are created annually as a byproduct of cheese production worldwide. About 34 million metric tons of whey are not economically utilized, and thus are discarded. The whey byproduct of cheese making, therefore, presents an inexpensive and ready source of immunoglobulins.

Numerous techniques are known to exist for producing dry concentrated protein extract from whey. This protein extract is commonly referred to as whey protein concentrate or "WPC." Such protein extraction and concentration techniques have been primarily concerned with preserving the food qualities of the WPC, such as taste, flavor, and solubility. Although these techniques are useful for producing food products, they almost universally destroy or substantially reduce the immunological activity of immunoglobulins in the concentrate by exposing the raw milk, whey, or protein concentrate to (1) excessive thermal (time and temperature) conditions, (2) excessive bacterial activity, or (3) excessive enzymes added in processing or resulting from bacterial activity.

Methods have been developed for separating immunologically active immunoglobulins from raw milk. U.S. Pat. Nos. 4,816,252 and 4,834,974 describe such methods, which are illustrative of methods that can be used for preparing an immunologically active immunoglobulin concentrate according to the present invention. Raw milk is first flash pasteurized to control microbial activity in the milk without significantly diminishing the immunological activity of the immunoglobulins in the milk. Next, the milk is exposed to an appropriate cheese starter culture, such as a lactobacillus, at carefully controlled temperatures and for limited times to achieve a selected degree of curd formation without significantly affecting the immunological activity of the immunoglobulins. The whey is then separated from the cheese curd and transferred to a clarifier or separator under carefully controlled conditions to remove fat and casein particles. The clarified whey is then subjected to ultrafiltration to remove or substantially reduce the amounts of small proteins, salts, and other non-protein materials in the retained protein concentrate or retentate. Ultrafiltration can be performed in stages to optimize purification of the immunglobulins. Optionally, other concentration and purification steps, such as reverse osmosis and ion exchange chromatography, can then be used to further improve the purity and concentration of the immunoglobulin concentrate while maintaining the immunological activity thereof. The immunoglobulin concentrate is then dried through conventional freeze-drying or spray drying methods. The resulting dry immunoglobulin concentrate can then be stored at room temperature. At least about 7% of the total solids of immunoglobulin concentrates prepared by these methods comprise immunologically active immunoglobulins. When ultrafiltration and ion exchange chromatography are both used in the purification procedure, the proportion of immunologically active immunoglobulins as a percentage of total solids can be increased to at least about 50%. Repeated ion exchange chromatography steps can further increase the proportion of immunologically active immunoglobulins as a percentage of total solids. U.S. Pat. Nos. 4,816,252 and 4,834,974 are hereby incorporated herein by reference as illustrative of methods for purifying immunologically active immunoglobulin concentrate. The present invention is not limited to these methods, however, and any method of purifying and concentrating immunologically active immunoglobulins from milk, whey, or another suitable source is to be considered within the scope of the invention as long as an effective amount of immunologically active immunogloblins is obtained in the "immunoglobulin composition." Bovine milk and bovine whey are preferred sources of immunoglobulins, but other species of animal could also be used.

A bacteria and whey-containing composition according to the present invention comprises a mixture of an immunoglobulin composition and a beneficial human intestinal bacterium, such as a lactobacillus or a bifidobacterium or mixtures thereof. The composition is made by mixing dry immunologically active immunoglobulins with dry beneficial human intestinal bacteria. The bacteria are prepared, for example, by culturing in a rich medium such as LB, J. Miller, Experiments in Molecular Genetics, Cold Spring Harbor Laboratory, Cold Spring Harbor, N.Y. (1972), until the late log phase of growth is reached. The bacteria are then concentrated and lyophilized according to standard methods.

The dry immunoglobulins and dry bacteria are then mixed in selected proportions. Just prior to consumption, the dry composition is reconstituted with water, juice, or the like to result in a smooth liquid composition that can be consumed orally.

It has been found that oral administration of such a bacteria and immunoglobulin-containing composition has a beneficial effect on gastrointestinal health. Although immunoglobulin compositions containing immunologically active immunoglobulins and beneficial bacteria such as lactobacilli and bifidobacteria each have some effect on diminishing the growth of pathogenic microorganisms in the gastrointestinal tract, it has been surprising to discover that a composition containing a mixture of the immunoglobulin composition and beneficial bacteria has a synergistic effect in causing death of the pathogenic microorganisms and in restoring gastrointestinal health. Regular consumption of the bacteria and immunoglobulin-containing composition has the effect of maintaining good gastrointestinal health. The bacteria and immunoglobulin-containing composition contains an effective amount of each of the bacterial and immunoglobulin components, and preferably contains weight ratios of bacteria to immunologically active immunoglobulins in the range of about 20:1 to about 1:20. More preferably, the weight ratios of bacteria to immunologically active immunoglobulins are in the range of about 1:5 to about 10:1.

The effects of exposing pathogenic microorganisms to bacteria and immunoglobulin-containing compositions according to the present invention are illustrated in the following examples. These examples are merely illustrative and are not intended to delimit the scope of the invention.

EXAMPLE 1

In vitro cultures of *Candida albicans* were prepared by subculturing from a stock culture in a rich liquid medium. Cultures were incubated at 37° C., and cells were counted by dilution and plating on plate count agar. FIG. 1 shows cell viability in cultures containing *C. albicans* alone (●) and cultures containing both *C. albicans* (♦) plus *L. acidophilus* strain NCFM (▲). During the course of this study, the *C. albicans* multiplied at the same rate regardless of the presence or absence of the *L. acidophilus* NCFM. The number of viable *L. acidophilus* NCFM cells, however, was diminished by a factor of about 20 in the presence of *C. albicans* cells.

EXAMPLE 2

Figure 2:
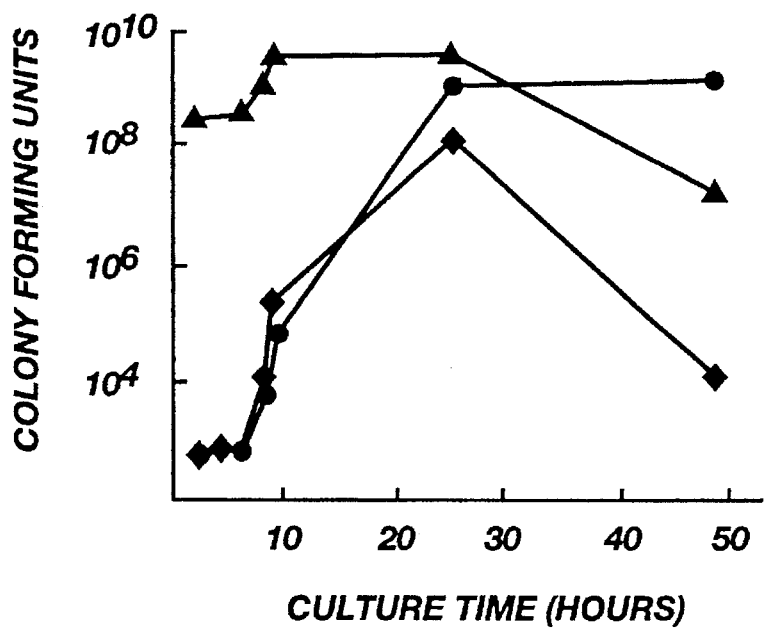
FIG. 2 shows growth curves for Candida (●) cultured alone, and for a mixed culture of Candida (♦) and *L. acidophilus* NCFM (▲) also containing an immunoglobulin composition according to the present invention.
Figure 3:
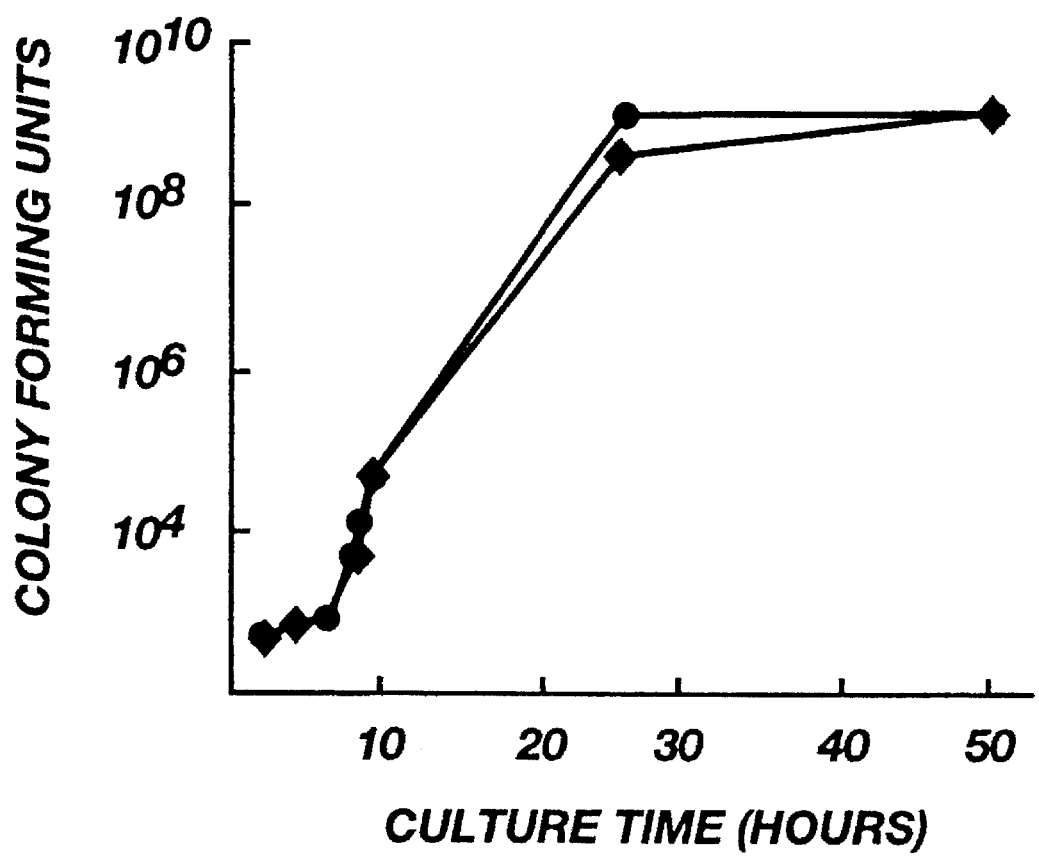
FIG. 3 shows growth curves for Candida (●) cultured alone, and for Candida (♦) cultured in the presence of an equal amount of immunoglobulin composition as in FIG. 2.

FIG. 2 shows the cell viability in cultures containing *C. albicans* alone (●) and cultures containing both *C. albicans* (♦) and *L. acidophilus* strain NCFM (▲) as in Example 1, with the exception that the immunoglobulin composition containing immunologically active immunoglobulins was added to the mixed cultures of *C. albicans* plus *L. acidophilus* strain NCFM in a weight ratio of 1 part of *L. acidophilus* strain NCFM to 5 parts of immunoglobulin composition. Two predominant differences occurred in this example compared to Example 1. First, the viability of *L. acidophilus* strain NCFM was enhanced by a factor of about 4 to 5 in the presence of the immunoglobulin composition as compared to cultures in which the immunoglobulin composition was absent. Second, the viability of *C. albicans* was greatly reduced after about 20 hours of co-culturing with *L. acidophilus* strain NCFM in the presence of the immunoglobulin composition. In other experiments, it has been found that the immunoglobulin composition by itself did not affect the viability of *C. albicans* (FIG. 3). Thus, although neither *L. acidophilus* strain NCFM nor the immunoglobulin composition alone affected the growth and viability of *C. albicans* in vitro, the mixture of *L. acidophilus* strain NCFM and the immunoglobulin composition caused a rapid decline in the viability of *C. albicans*. Further, the growth and viability of *L. acidophilus* strain NCFM was enhanced in co-culture with *C. albicans* in the presence of the immunoglobulin composition as compared to when the immunoglobulin composition was absent. These results were unforeseen, i.e. that the combination of beneficial bacteria and immunoglobulins would yield a better result than the additive effects of the bacteria and the immunoglobulins, and that the immunoglobulins would improve the viability of the bacteria in co-culture with another microorganism. Further, these results were considered predictive of what would occur in vivo since lactobacilli are known to survive in the gastrointestinal tract and immunoglobulins have been shown to provide passive immunity to certain pathogens upon oral administration.

EXAMPLE 3

In vitro cultures of *Salmonella typhimurium* were prepared by subculturing from a stock culture in a rich liquid medium, J. Miller, Experiments in Molecular Genetics, Cold Spring Harbor Laboratory, Cold Spring Harbor, N.Y. (1972). Cultures were incubated at 37° C., and cells were counted by dilution and plating on plate count agar.

Figure 4:
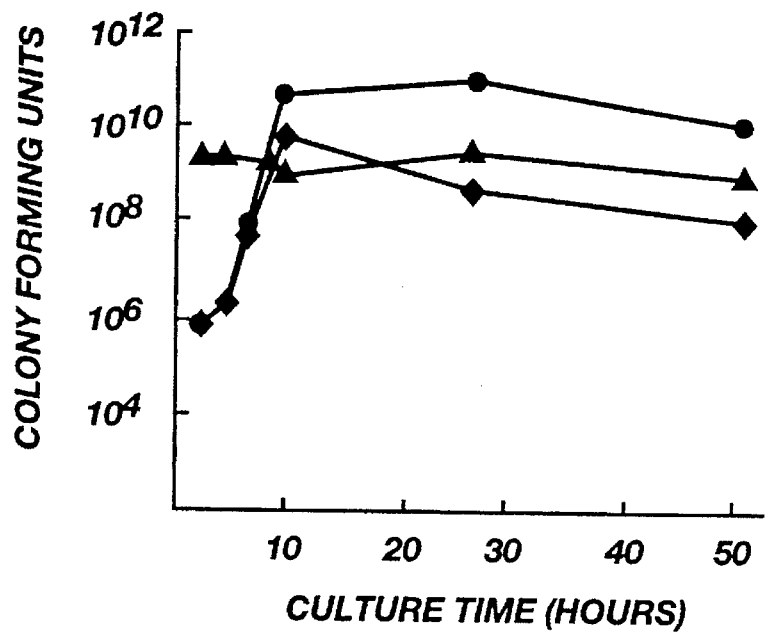
FIG. 4 shows growth curves for *S. typhimurium* (●) cultured alone, and for a mixed culture of *S. typhimurium* (♦) and *L. acidophilus* NCFM (▲).

FIG. 4 shows growth curves for cultures containing *S. typhimurium* alone and cultures containing *S. typhimurium* plus *L. acidophilus*. Cultures containing *S. typhimurium* (●) alone reached stationary phase with a maximum number of viable cells after about 10 hours of growth. Cultures containing a mixture of *S. typhimurium* and *L. acidophilus* strain NCFM also resulted in maximum numbers of viable cells of *S. typhimurium* (♦) at about 10 hours, although the number of viable cells was diminished about 100-fold compared to *S. typhimurium* cultured alone. The cell viability of *L. acidophilus* strain NCFM (▲) appeared to unaffected by the presence of *S. typhimurium*.

EXAMPLE 4

Figure 5:
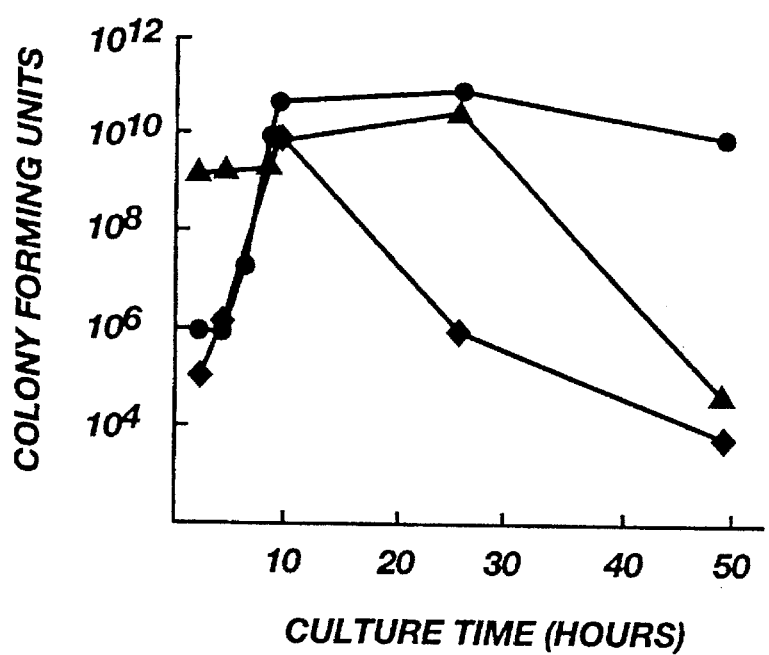
FIG. 5 shows growth curves for *S. typhimurium* (●) cultured alone, and for a mixed culture of *S. typhimurium* (♦) and *L. acidophilus* NCFM (▲) also containing an immunoglobulin composition according to the present invention.

FIG. 5 shows the cell viability in cultures containing *S. typhimurium* alone (●) and cultures containing both *S. typhimurium* (♦) plus *L. acidophilus* strain NCFM (▲) as in Example 4 with the exception that the immunoglobulin composition containing immunologically active immunoglobulins was added to the mixed cultures of Candida plus *L. acidophilus* strain NCFM in a weight ratio of 1 part of *L. acidophilus* strain NCFM to 5 parts of immunoglobulin composition. These results show that when *S. typhimurium* is cultured in the presence of both *L. acidophilus* strain NCFM and whey immunoglobulins, the *S. typhimurium* failed to produce as many viable cells after 10 hours of growth, and the viability of *S. typhimurium* was greatly reduced through the duration of the experiment as compared to growth in co-culture with *L. acidophilus* strain NCFM without the immunoglobulins. Therefore, the mixture of *L. acidophilus* strain NCFM and the immunoglobulin composition greatly decreased the viability of *S. typhimurium* in vitro compared to growth in the presence of either the immunoglobulin composition or *L. acidophilus* strain NCFM alone. There appears to be an unexpected synergistic effect in diminishing *S. typhimurium* viability by combining the immunoglobulin composition and *L. acidophilus*.

EXAMPLE 5

A strain of *E. coli* isolated from human intestine was cultured alone, in the presence of *L. acidophilus* strain NCFM, and in the presence of both *L. acidophilus* strain NCFM and the immunoglobulin composition in a weight ratio of about 1:10. The results were similar to those of Examples 4 and 5, wherein the viability of the *E. coli* was greatly diminished in the presence of both *L. acidophilus* strain NCFM and the immunoglobulin composition as compared to in the presence of either alone.

The composition of the present invention can be used for maintaining gastrointestinal health as well as for treating diarrhea, constipation, and other types of gastrointestinal distress due to infection with pathogenic microorganisms such as *E. coli*, Salmonella, Candida, rotavirus, and Cryptosporidium by orally administering an effective amount of the composition. The effective amount will vary depending on the size and age of the individual, whether the selected effect is to maintain gastrointestinal health or to restore gastrointestinal health from distress due to infection with a pathogenic microorganism, the particular pathogenic microorganism involved, and the like. A person skilled in the art can routinely determine such an effective amount. The dry ingredients of the composition are stirred into water or juice, and the resulting suspension is taken by mouth. Preferably, dosage is in the range of about 1 to about 100 mg/kg of body weight. More preferably, dosage is in the range of about 5 to about 50 mg/kg of body weight. Doses of the bacteria and immunoglobulin-containing composition can be divided, wherein two or administrations of divided doses are used to deliver a complete dose. Multiple doses can also be administered, but it is recommended that daily consumption be limited to 1 to 3 doses.

EXAMPLE 6

An adult afflicted with diarrhea due to infection with Salmonella was treated with a composition according the present invention containing about 5 parts by weight of *L. acidophilus* NCFM and about 1 part by weight of an immunoglobulin composition comprising concentrated immunologically active immunoglobulins purified from bovine whey. Doses of about 10 mg/kg of body weight were taken by mouth 3 times daily by stirring into water or juice and drinking the resulting suspension. Symptoms began to subside within 24 hours and had completely disappeared within 3 days.

EXAMPLE 7

A small child afflicted with diarrhea due to rotavirus infection was treated with a composition according the present invention containing 5 parts by weight of *B. adolescentis* and 1 part by weight of an immunoglobulin composition comprising concentrated immunologically active immunoglobulins purified from bovine whey. A dose of about 20 mg/kg of body weight was taken by mouth once daily by stirring into water or juice and drinking the resulting suspension. Symptoms began to subside within 24 hours and had completely disappeared within 3 days.

EXAMPLE 8

An adult afflicted with diarrhea due to infection with Cryptosporidium is treated with a composition according the present invention containing a weight ratio of about 5:1 of *L. acidophilus* NCFM to concentrated immunologically active immunoglobulins purified from bovine whey. Doses of about 10 mg/kg of body weight are taken by mouth 3 times daily by stirring into water or juice and drinking the resulting suspension. Good gastrointestinal health is restored.

EXAMPLE 9

An adult afflicted with diarrhea due to infection with Candida is treated with a composition according to the present invention containing a weight ratio of about 1:5 of *B. adolescentis* to concentrated immunologically active immunoglobulins purified from bovine whey. Doses of about 5 mg/kg of body weight are taken by mouth 3 times daily by stirring into water or juice and drinking the resulting suspension. Good gastrointestinal health is restored.

EXAMPLE 10

An adult who averages 10 episodes of gastrointestinal distress per year takes a daily dose of about 50 mg/kg of body weight of a 5:1 weight ratio of the bacteria and immunoglobulin-containing composition according to the present invention with water or juice. In the ensuing year, only 1 episode of gastrointestinal distress is experienced. This example shows that not only can the bacteria and immunoglobulin-containing composition of the present invention be used for treating acute cases of gastrointestinal distress, but is also effective as a dietary supplement in maintaining good gastrointestinal health.

EXAMPLE 11

Various formulations of the bacteria and immunoglobulin-containing composition are tested in treating acute episodes of gastrointestinal distress, as summarized in Table 1.

TABLE 1

| Bacteria[a] | Immunoglobulins[a] | Condition | Result[b] |
|---|---|---|---|
| 0.2 | 1 | diarrhea | +++ |
| 0.2 | 25 | diarrhea | + |
| 5 | 1 | diarrhea | + |
| 5 | 25 | diarrhea | +++ |
| 0.1 | 100 | diarrhea | − |
| 100 | 0.1 | diarrhea | − |
| 0.5 | 2.5 | diarrhea | +++ |
| 0.5 | 10 | diarrhea | +++ |
| 2 | 2.5 | diarrhea | +++ |
| 2 | 10 | diarrhea | +++ |
| 1 | 4 | constipation | +++ |
| 4 | 1 | constipation | ++ |
| 1 | 3 | gas/cramps | +++ |
| 3 | 1 | gas/cramps | ++ |

[a]Parts by weight.
[b]Symbols represent a relative scale for restoring gastrointestinal health: +++, excellent; ++, very good; +, good; −, poor.

We claim:

1. A bacteria and immunoglobulin-containing composition for promoting gastrointestinal health comprising
   (a) an effective amount of a beneficial human intestinal microorganism; and
   (b) an effective amount of an immunoglobulin composition comprising concentrated immunologically active immunoglobulins.

2. The composition of claim 1 wherein said beneficial human intestinal microorganism is selected from the group consisting of lactobacilli and bifidobacteria.

3. The composition of claim 2 wherein the weight ratio of beneficial human intestinal microorganism to immunologically active immunoglobulins is in the range of about 20:1 to about 1:20.

4. The composition of claim 3 wherein weight ratio of beneficial human intestinal microorganism to immunologically active immunoglobulins is in the range of about 1:5 to about 10:1.

5. The composition of claim 4 wherein said beneficial human intestinal microorganism is a lactobacillus.

6. The composition of claim 5 wherein said lactobacillus is selected from the group consisting of *L. acidophilus, L. bulgaricus, L. casei, L. fermentum, L. salivaroes, L. brevis, L. leichmannii, L. plantatum,* and *L. cellobiosus.*

7. The composition of claim 6 wherein said lactobacillus is *Lactobacillus acidophilus.*

8. The composition of claim 7 wherein said *Lactobacillus acidophilus* is strain NCFM.

9. The composition of claim 4 wherein said beneficial human intestinal microorganism is a bifidobacterium.

10. The composition of claim 9 wherein said bifidobacterium is selected from the group consisting of *Bifidobacterium adolescentis, B. infantis, B. iongum, B. thermophilum,* and *B. bifidum.*

11. The composition of claim 10 wherein said bifidobacterium is *B. adolescentis.*

12. The composition of claim 1 wherein said immunoglobulin composition further comprises a carrier.

13. The composition of claim 12 wherein said carrier comprises at least one member selected from the group consisting of a carbohydrate and a lipid, wherein said carbohydrate is capable of being an energy source for said beneficial human intestinal microorganism and said lipid aids in reconstitution of said immunoglobulin composition.

14. The composition of claim 13 wherein said carbohydrate comprises maltodextrin and said lipid comprises lecithin.

15. The composition of claim 1 wherein said immunoglobulin composition is purified from a source selected from the group consisting of milk, milk products, and whey.

16. The composition of claim 15 wherein said source is bovine.

17. A method of restoring and maintaining gastrointestinal health comprising the step of orally administering a bacteria and immunoglobulin-containing composition comprising an effective amount of a beneficial human intestinal microorganism and an effective amount of an immunoglobulin composition comprising concentrated immunologically active immunoglobulins.

18. The method of claim 17 wherein said beneficial human intestinal microorganism is selected from the group consisting of lactobacilli and bifidobacteria.

19. The method of claim 18 wherein the weight ratio of beneficial human intestinal microorganism to immunologically active immunoglobulins is in the range of about 20:1 to about 1:20.

20. The method of claim 19 wherein the weight ratio of beneficial human intestinal microorganism to immunologically active immunoglobulins is in the range of about 1:5 to about 10:1.

21. The method of claim 20 wherein said beneficial human intestinal microorganism is a lactobacillus.

22. The method of claim 21 wherein said lactobacillus is selected from the group consisting of *L. acidophilus, L. bulgaricus, L. casei, L. fermentum, L. salivaroes, L. brevis, L. leichmannii, L. plantatum,* and *L. cellobiosus.*

23. The method of claim 22 wherein said lactobacillus is *Lactobacillus acidophilus.*

24. The method of claim 23 wherein said *Lactobacillus acidophilus* is strain NCFM.

25. The method of claim 20 wherein said beneficial human intestinal microorganism is a bifidobacterium.

26. The method of claim 25 wherein said bifidobacterium is selected from the group consisting of *Bifidobacterium adolescentis, B. infantis, B. iongum, B. thermophilum,* and *B. bifidum.*

27. The method of claim 26 wherein said bifidobacterium is *B. adolescentis.*

28. The method of claim 17 wherein said immunoglobulin composition further comprises a carrier.

29. The method of claim 28 wherein said carrier comprises at least one member selected from the group consisting of a carbohydrate and a lipid, wherein said carbohydrate is capable of being an energy source for said beneficial human intestinal microorganism and said lipid aids in reconstitution of said immunoglobulin composition.

30. The method of claim 29 wherein said carbohydrate comprises maltodextrin and said lipid comprises lecithin.

31. The method of claim 17 wherein said immunoglobulin composition is purified from a source selected from the group consisting of milk, milk products, and whey.

32. The method of claim 31 wherein said source is bovine.

33. The method of claim 17 wherein said step of orally administering said bacteria and immunoglobulin-containing composition modulates infection by a pathogenic microorganism that results in gastrointestinal distress.

34. The method of claim 33 wherein said pathogenic microorganism is selected from the group consisting of bacteria, viruses, fungi, and protozoa.

35. The method of claim 34 wherein said pathogenic microorganism is selected from the group consisting of *E. coli,* Salmonella, Candida, Cryptosporidium, and rotavirus.

* * * * *